United States Patent [19]
McKinnon et al.

[11] Patent Number: 6,068,377
[45] Date of Patent: May 30, 2000

[54] VISUAL TEST UTILIZING COLOR FREQUENCY DOUBLING

[75] Inventors: Stuart James McKinnon, Ellicott City, Md.; Scott Laird Whittenburg, New Orleans, La.; Jeffrey L. Stewart, Greenwich, Conn.

[73] Assignee: VisionRx.Com, Inc., Elmsford, N.Y.

[21] Appl. No.: 09/312,294

[22] Filed: May 14, 1999

[51] Int. Cl.[7] ..................................................... A61B 3/10
[52] U.S. Cl. ............................................. 351/221; 351/246
[58] Field of Search ..................................... 351/205, 211, 351/222, 246; 600/399, 401, 558; 128/898

[56] References Cited

U.S. PATENT DOCUMENTS 5,065,767  11/1991  Maddess ................................. 128/898
5,539,482  7/1996  James et al. ........................... 351/246
5,912,723  6/1999  Maddess ................................. 351/246

*Primary Examiner*—George Manuel
*Attorney, Agent, or Firm*—John de la Rosa

[57] ABSTRACT

A novel psychophysical visual test is proposed for testing a person for glaucoma, and based on the discovery that a frequency doubling phenomenon is produced by isoluminent color visual stimuli. More specifically, it is proposed to construct a visual stimulus for which alternating colors in a grating pattern is the only basis for producing the frequency doubling phenomenon. That is, the colors are of the same luminance or intensity level, i.e., isoluminent, but each grating or pattern alternates from one color to another. Preferably, the colors are complementary color pairs, such as blue and yellow.

86 Claims, 4 Drawing Sheets

FIG. 3
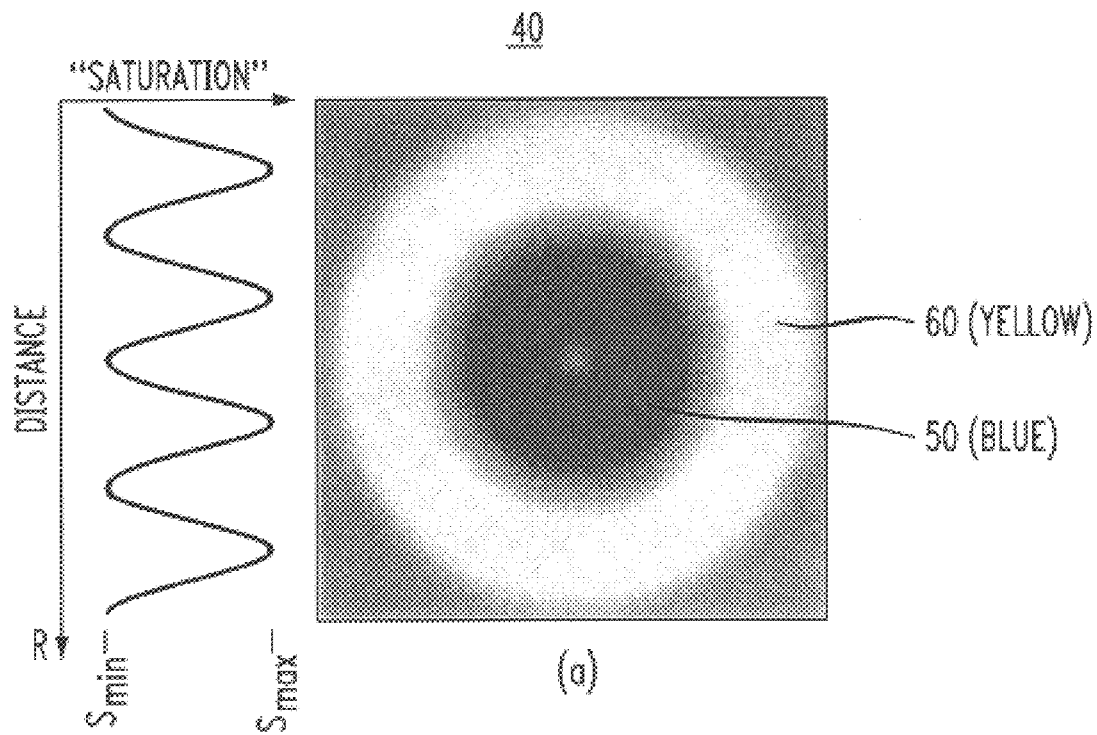
(a)
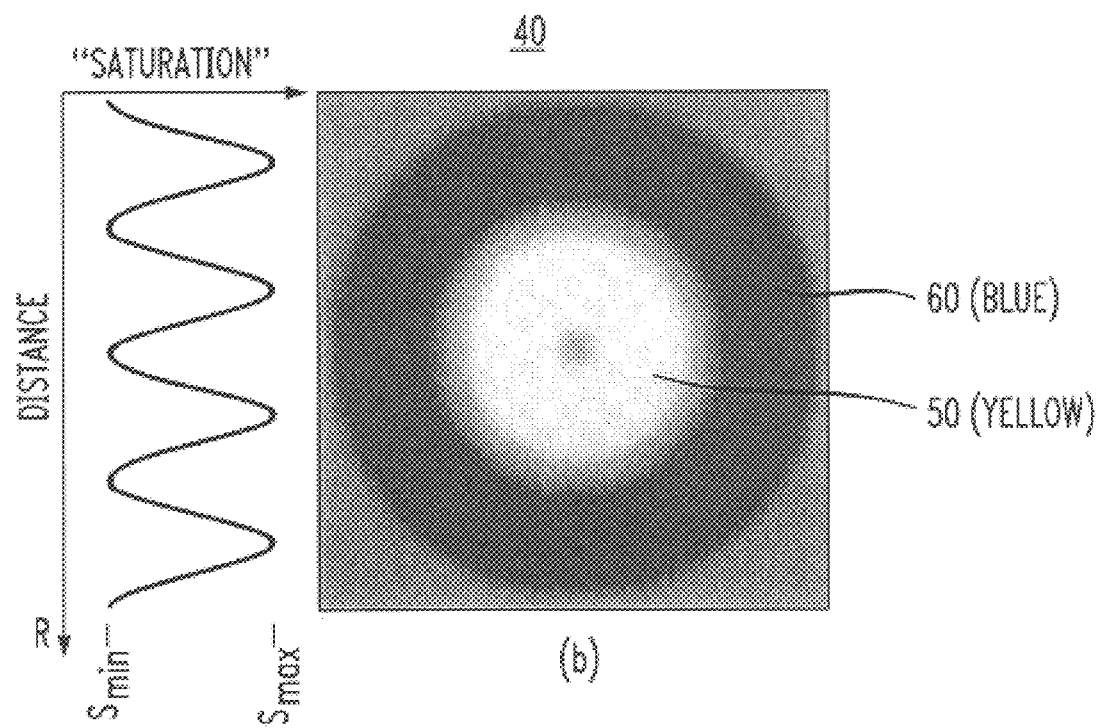
(b)

VISUAL TEST UTILIZING COLOR FREQUENCY DOUBLING

TECHNICAL FIELD

The present invention relates to visual test systems, and more particularly, to visual test systems which utilize a spatial frequency doubling phenomenon for the early detection of glaucoma.

BACKGROUND OF THE INVENTION

Glaucoma is one of the leading causes of blindness, resulting from the loss of a particular type of retinal cells, more specifically, retinal ganglion cells (RGC). Axons of the ganglion cells project out of the eye to form the optic nerve. With the loss of ganglion cells, the optic nerve which connects the retina to the brain is gradually destroyed, and results in blindness if the disease is not treated early enough.

Although typical signs of glaucoma include a scotoma as well as a "cupping" of the optical disc, by the time such signs are detected, treatment is unlikely to be successful. While glaucoma is typically associated with an elevation in a patient's intraocular tension, testing for such an elevation is generally unreliable. This is so, since an elevated intraocular tension typically occurs transiently in the morning and evening, or may not even be exhibited by some patients.

As such, an evaluation of the patient's visual field has long been the method used for the clinical diagnosis of glaucoma, as well as other pathologies. For example, in so-called "white-on-white" perimetry, a white test object of varying contrast is displayed against a white background at different points in the patient's visual field. The characteristic locations where the test object is undetected for a particular contrast allow clinicians not only to diagnose, but also to determine the severity of the glaucoma. A drawback, however, to this approach is its lack of sensitivity, typically detecting glaucoma only after 30–50% of retinal ganglion cells have been lost or destroyed.

Efforts to improve the sensitivity of the above latter approach have focused on the physiology of retinal ganglion cells. For example, in "short-wave" automated perimetry (SWAP), a blue rather than a white test object is displayed within the patient's visual field, and against a yellow background. The characteristic locations where the test object is undetected for a particular contrast are used to effectively screen patients for glaucoma damage.

Recently, another approach using the phenomenon of so-called "frequency doubling" has also been used for the early detection of glaucoma. See, for example, U.S. Pat. No. 5,065,767, which is incorporated herein by reference. As shown in FIG. 1, in this latter approach, a sinusoidal grating pattern 10 consisting of light and dark bars or striations 20, 30, respectively, is modulated at a temporal frequency between 10 and 50 Hz. That is, the bars are contrast modulated in a sinusoidal fashion from white through gray to black at about 10 to 50 times a sec. At such frequencies, typically about 20 Hz, the grating pattern is perceived by patients to have double the spatial frequency. For a discussion on this phenomenon, see, for example, D. H. Kelly, "Frequency Doubling In Visual Response," *J. Opt. Soc. Am.*, 56:1628–33 (1966); and D. H. Kelly, "Nonlinear Visual Responses To Flickering Sinusoidal Gratings," *J. Opt. Soc. Am.* 1051–55 (1981).

Patients suffering from glaucoma typically require twice the contrast level between the white and black bars before observing the above frequency doubling phenomenon. This phenomenon is now understood to be a non-linear visual response of the eye. Importantly, this difference in visual response between patients with normal vision and those suffering from glaucoma is used to detect the disease at an earlier stage.

Although the above latter approaches perform satisfactorily, it would still be desirable to have a glaucoma test which has greater sensitivity, so as to detect glaucoma at its earliest possible stage.

SUMMARY OF THE INVENTION

A novel psychophysical visual test is proposed for testing a person for glaucoma, and based on the discovery that the frequency doubling phenomenon noted herein above is also produced by isoluminent color visual stimuli. More specifically, it is proposed to construct a visual stimulus for which alternating colors in a grating pattern is the only basis for producing the frequency doubling phenomenon. That is, the colors are of the same luminance or intensity level, i.e., isoluminent, but each grating alternates from one color to another. Preferably, the colors are complementary color pairs, such as blue and yellow.

In one embodiment, the color visual stimulus consists of two circular gratings. Although the luminance level remains constant, the color of each grating alternates between blue and yellow at about 10–50 times a sec, with the "saturation" or "purity" of each color varying sinusoidally radially inward. When the colors are alternated in this latter manner, the stimulus is perceived to have double the spatial frequency. Persons suffering from glaucoma, however, find it more difficult to detect this frequency-doubled stimulus. Observation thresholds to this stimulus can be measured by reducing the difference in the "saturation" or purity levels of the colors (saturation modulation depth) until the visual stimulus disappears, and used beneficially to detect for the presence of glaucoma.

One method to determine the threshold value or level at which the frequency-doubled stimulus is not observed is a modified binary staircase algorithm that involves (i) reducing the saturation modulation depth by one-half of the previous value until no visual stimulus is observed; and then (ii) increasing the modulation depth in predetermined incremental steps until the frequency-doubled stimulus is again perceived. Taking the average value then precisely determines the threshold level.

To diagnose more accurately for glaucoma, however, a visual mapping of the patient's visual field or peripheral vision is more preferable. Characteristic locations where the frequency-doubled stimulus is undetected may allow clinicians not only to diagnose, but also to determine the severity of the glaucoma. Accordingly, it is preferable to record the patient's response to the color stimulus as the stimulus is displayed throughout the patient's visual field. To perform such a visual perimetry, a computer may be programmed to display the color visual stimulus at various locations on a color monitor, corresponding to different visual field locations. Importantly, the colors of the circular grating in the stimulus each alternates synchronously between yellow and blue at a desired temporal frequency. In addition to displaying the color visual stimulus, the computer monitors the patient's response to the stimulus as the saturation modulation depth is varied, which response may be entered by pressing a button, such as on a computer mouse. In this manner, a visual mapping of the patient's retina is then provided.

BRIEF DESCRIPTION OF THE DRAWINGS

The features and advantages of the present invention will become more readily apparent from the following detailed description of the invention in which like elements are labeled similarly and in which:

FIG. 3 depicts an embodiment of a color visual stimulus consisting of isoluminent circular color gratings, one blue and one yellow, in accordance with the principles of the invention;

DETAILED DESCRIPTION

In accordance with the principles of the invention, a novel psychophysical test utilizing the frequency doubling phenomenon is proposed which may be more sensitive to the loss of retinal ganglion cells than conventional visual field perimetric techniques. The present invention is based on the discovery that the frequency doubling phenomenon noted herein above is also produced by isoluminent color visual stimuli, due to a subset of $M_y$ ganglion cells present in the retina previously unreported to respond to such stimuli. As such, the present invention uniquely recognizes that this color stimulus-response of $M_y$ cells may be used to produce the frequency doubling phenomenon for the early detection of glaucoma.

To better understand the aspects of the present invention, it would be beneficial to examine briefly the physiology of the retina. Two types of ganglion cells are present in the retina, namely large magnocellular ("MC") cells and small parvocellular ("PC") cells, each of which responds differently to visual stimuli. Magnocellular cells respond rapidly to a visual stimulus, and consist of larger "y-type" ("$M_y$") and smaller "x-type" ("$M_x$") cells. There are, however, significantly fewer $M_y$ cells than $M_x$ cells, with the $M_y$ cells primarily linked to the non-linear visual response of the retina. On the other hand, PC ganglion cells respond slowly to a visual stimulus.

Earlier experimental work has shown that the large MC ganglion cells are affected first in patients with glaucoma, equally affecting both the $M_x$ and $M_y$ cells, but have been unreported to respond to isoluminent color visual stimuli. Conventional frequency doubling perimetry is ostensibly based on the fact that the loss of the larger MC ganglion cells has a greater affect on the retina's non-linear visual response, and that such MC ganglion cells respond quickly to only changes in luminance or intensity. As such, it is known that patients with glaucoma have a different visual response to a modulated sinusoidal black and white grating pattern, and, thus, observe the above frequency doubling phenomenon at different contrast levels.

Figure 1:
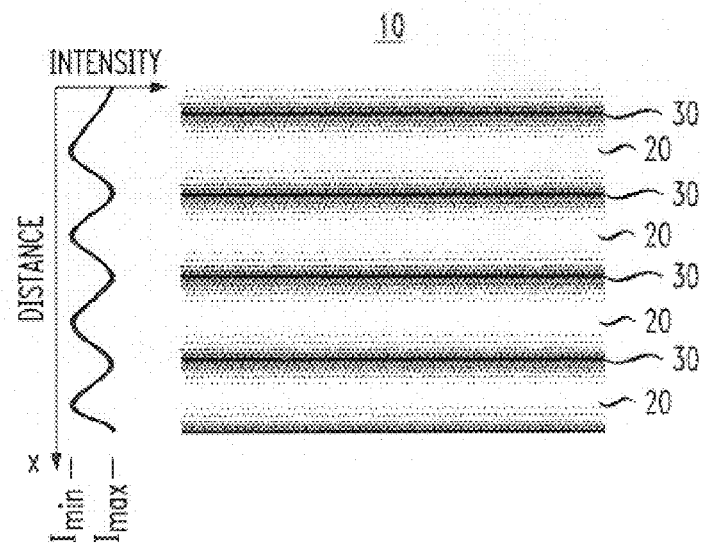
FIG. 1 depicts a sinusoidal grating of the prior art consisting of white to black bars which when modulated at a temporal frequency of 10–50 Hz is observed as having double the spatial frequency.
Figure 2:
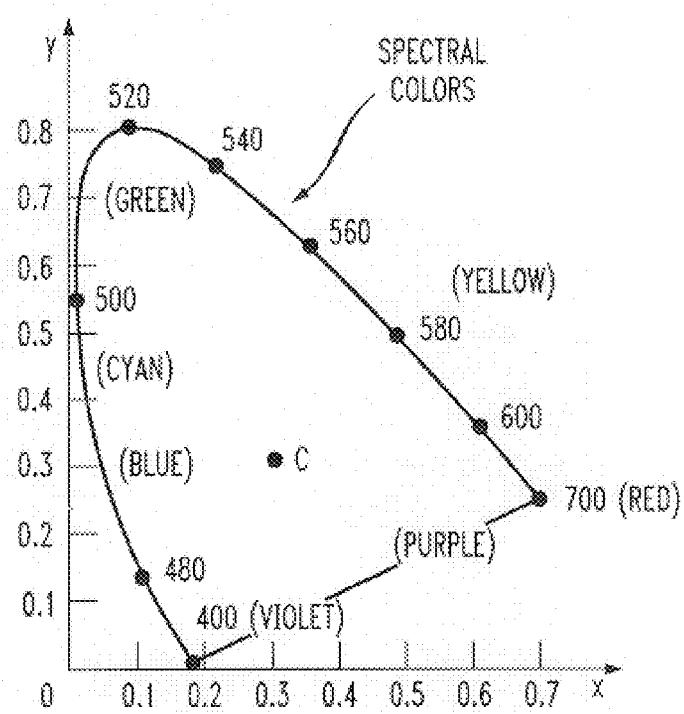
FIG. 2 depicts the CIE chromaticity diagram.

In accordance with the principles of the invention, it is proposed, however, to construct a visual stimulus for which alternating colors in a grating pattern is the only basis for producing the frequency doubling phenomenon. That is, the colors are of the same luminance or intensity level, i.e., isoluminent. Preferably, the colors are complementary colors which when combined produce white light. Examples of complementary color pairs are red and cyan, green and magenta, and blue and yellow. Other complementary colors may be obtained by reference, for example, to the CIE chromaticity diagram shown in FIG. 2. Points along the curve are the "pure" colors, with point C in the diagram corresponding to white. Complementary colors are represented on this chromaticity diagram as two color pairs situated on opposite sides of C and connected with a straight line. Similarly, in other color system models, the complementary colors are 180° degrees apart, such as in the RGB, HSV and HSL color models, among others.

Referring to FIG. 3, there is shown one embodiment of a color visual stimulus 40 consisting of two circular gratings 50, 60, here having two spatial cycles. Although the luminance level remains constant, the color of each grating alternates preferably between two colors at a frequency $f_s$ of about 10–50 times a sec, preferably 20. In other words, each grating synchronously switches back and forth between the two colors at the desired frequency, here the complementary color pair of blue and yellow.

For example, in FIGS. 3(a)–(b), circular grating 50 is first blue then yellow, whereas circular grating 60 is yellow then blue. However, at any instance in time, the "saturation" or "purity" of each color varies sinusoidally radially inward, ranging from a maximum to a minimum, as further depicted in FIG. 3. Thus, near the edges of each grating, each color appears pale or gray.

Throughout this specification, the term saturation or purity refers to the amount of dilution of the pure color or hue with neutral gray of the same luminance, as commonly used in the field of colorimetry. In some chromaticity diagrams or color systems, this latter characteristic of color is known as chroma. Furthermore, the term "saturation modulation depth" M is defined herein as a functional relationship of the maximum and minimum saturation levels using the equation:

$$M = \frac{(S_{\max} - S_{\min})}{(S_{\max} + S_{\min})}$$

where $S_{max}$ is the maximum saturation level and $S_{min}$ is the minimum saturation level. See, for example, FIG. 2.

When the colors in color visual stimulus 40 are alternated at a frequency between 10–50 Hz, frequency doubling causes four cycles to be perceived, instead of two, if the visual stimulus is observed. Persons suffering from glaucoma, however, find it more difficult to observe this frequency-doubled stimulus. Observation thresholds for this stimulus can be measured by reducing the difference in the "saturation" or purity of the colors or the modulation depth until the visual stimulus disappears. This is based on the reasoning that a diffuse loss in the $M_y$ cells at the onset of glaucoma would raise the observation threshold, and hence can be used to screen patients for glaucoma.

Preferably, color visual stimulus 40 is viewed monocularly from a distance at which it subtends about 1.5 degrees of visual angle, thereby providing a spatial frequency of about 1.3 cycles per degree of visual angle. There is a functional relationship, however, between the temporal and spatial frequencies at which frequency doubling is observed. Accordingly, it may be desirable in certain instances to use another spatial frequency, which can be readily accomplished by judiciously selecting the dimensions of the color gratings, as well as the distance from which the stimulus is observed. Preferably, the spatial frequency should fall within the range from about 0.25 to 5 cycles per degree of visual angle for frequencies greater than about 7 Hz for a person to observe the frequency doubling phenomenon.

Although linear gratings may also be used, circular gratings are preferable inasmuch as data collected using such gratings may be readily compared, for example, to perimetry techniques that employ circular test objects, such as Humphrey, Octopus, and Dicon perimeters, among others. The form of the gratings is not critical, except that each should preferably be of the same shape.

In view of the above, a visual technique to test a person for glaucoma comprises displaying color visual stimulus 40 to the person, with the color of each circular grating 50, 60 alternating synchronously between blue and yellow at a temporal frequency or rate of about 10–50 Hz. The difference in the saturation levels of the colors or modulation depth is such that the person observes a frequency-doubled pattern. Persons suffering from the loss of PC ganglion cells as a result of glaucoma, as well as other pathologies, will be unable to detect the visual stimulus as the modulation depth for the colors is reduced. Therefore, the present technique further comprises reducing the saturation modulation depth of the colors below a threshold level where the visual stimulus is no longer observed by the person. Comparing the threshold level against those of persons with normal vision should enable a clinician to screen persons with glaucoma, as well as other pathologies.

It should be clearly understood that as the difference in the saturation levels is reduced below the threshold level, no visual stimulus whatsoever is observed, and not just the frequency doubling phenomenon. As such, the person either observes the visual stimulus as having double the spatial frequency, or observes no visual stimulus whatsoever.

Inasmuch as the difference in saturation levels or modulation depth is used to detect for glaucoma, it is important to accurately determine the threshold value or level at which the visual stimulus is not observed. For this purpose, a modified binary staircase algorithm is preferred, and involves (i) reducing the saturation difference level or modulation depth by one-half of the previous value until the visual stimulus is not observed; and then (ii) increasing the saturation modulation depth in predetermined incremental steps until the frequency-doubled stimulus is perceived so as to determine precisely the threshold level. The average threshold is then used as the threshold modulation depth at which the person no longer observes color visual stimulus 40. Alternatively, the saturation modulation depth may be first increased by one-half, and then decreased in predetermined increments.

Note that the use of a blue-yellow color grating pattern has the advantage of not only testing for the loss of $M_y$ ganglion cells, but also for blue-yellow PC ganglion cells, which are believed to be lost at a significantly higher rate than red-green PC cells at the onset of glaucoma. Although PC ganglion cells respond slowly to luminance changes, their response is also believed to improve greatly with a color stimulus of higher frequency, such as color visual stimulus 40. Moreover, blue-yellow ganglion cells cover a larger receptive field on the retina. As such, the color frequency doubling visual test of the present invention should have greater sensitivity than other visual field test techniques.

Thus, based on our understanding of the physiology of the retina, it is anticipated that persons having normal vision and those suffering from glaucoma will have different visual responses to the above color visual stimulus, with glaucoma patients requiring a greater degree of saturation or purity difference between the colors before perceiving the frequency-doubled stimulus. It is not yet clear, however, whether such a visual response difference will be significantly more sensitive than conventional techniques.

To diagnose more accurately for glaucoma, however, it is particularly important to obtain a visual mapping of the patient's visual field or peripheral vision. Characteristic locations where the visual stimulus is undetected may allow clinicians not only to diagnose, but also to determine the severity of the glaucoma. Accordingly, it is preferable to record the patient's response to the color stimulus as the stimulus is displayed throughout the patient's visual field, using one eye at a time. In particular, the patient's central vision should be fixated while color visual stimulus 40 is displayed in a random fashion at different locations within the patient's visual field. To perform such a visual field perimetry, either static or kinetic, a patient preferably will be required to move a cursor into a fixation target which is displayed on a computer monitor, as discussed more fully herein below. Alternatively, the moving fixation technique disclosed in U.S. Pat. No. 5,565,949 may be employed, which is incorporated herein by reference. Other fixation techniques, of course, may be used, such as so-called "blind spot monitoring," among others.

Once having established fixation, color visual stimulus 40 will be displayed in a random fashion at each of the desired points within the patient's visual field. Note that the color visual stimulus may be displayed at either preprogrammed or manually selected locations within the patient's visual field, depending on the type of testing to be performed.

Upon responding to color visual stimulus 40, the cursor may then be automatically positioned outside the fixation target for the patient again to position the cursor inside the fixation target before displaying the next stimulus at another visual field location. Using the above described binary staircase algorithm, color visual stimulus 40 is displayed at the same location, but at different times until the saturation modulation depth reaches the threshold level where the visual stimulus is not seen. Note that in so-called "suprathreshold" testing, however, the color stimulus is only shown once at each visual field location. In this latter case, color visual stimuli are displayed with a predetermined modulation depth level, such as the level expected for persons with normal vision.

In order to ensure, however, that the results of this novel color frequency doubling perimetry can be readily compared to the accepted standards of automated perimetry, it is preferable to display color visual stimulus 40 at each of the 54 grid points of the standard 24-2 test pattern wherein each grid point is spaced about 6 degrees of visual field. The number of stimuli, their locations and the difference in the saturation levels, however, may be chosen in a different manner, depending on the test strategy that is to be employed. For example, in the above mentioned "suprathreshold" testing a lower number of visual field locations may be used to reduce the test time.

Also, to ensure reliability in the patient's response, false-positive and false-negative visual stimuli may be presented to the patient, such techniques being well known to those skilled in the art. In the former case, a blank stimulus is displayed, whereas in the latter a stimulus is displayed having a saturation modulation depth higher than the one previously displayed at the same visual field location.

Figure 4:
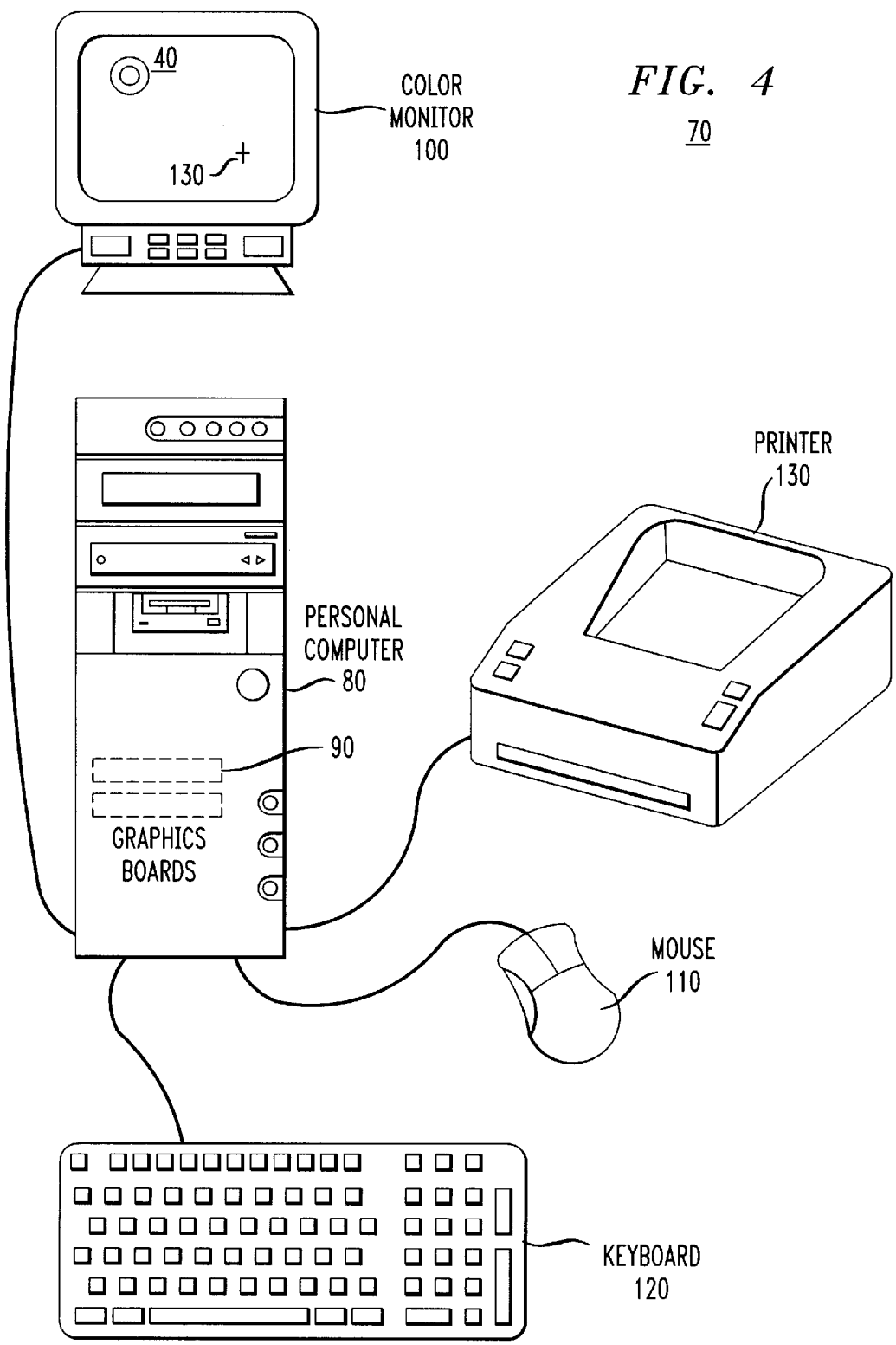
FIG. 4 depicts a simplified block diagram of a visual test system which may be employed to perform color frequency doubling perimetry in accordance with the principles of the invention.

Inasmuch as the present invention also encompasses an apparatus for performing the above inventive visual test, shown in FIG. 4 is a simplified block diagram of a color frequency doubling perimeter 70 in accordance with the principles of the invention. Color frequency doubling visual test system 70 comprises a computer 80, such as a personal computer (PC) running under Windows. Computer 80 includes conventional graphics boards 90 which may be readily programmed to display color visual stimulus 40 at various locations on a color monitor 100 corresponding to different visual field locations. Importantly, the colors of circular gratings 50, 60 in the stimulus each alternates between yellow and blue at a frequency of 10–50 Hz. In addition to displaying color visual stimulus 40, computer 80 monitors the patient's response which is entered by pressing a button, such as on a computer mouse 110, or alternatively entered using voice recognition.

Figure 5:
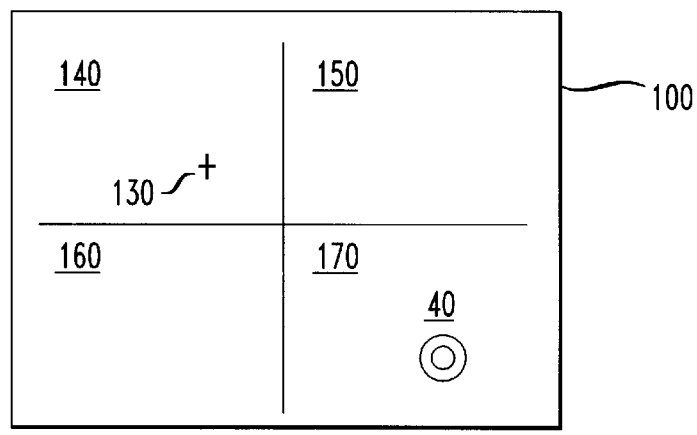
FIG. 5 depicts the screen of the color monitor of FIG. 3, which has been broken into four quadrants.

In this preferred embodiment, the patient views color monitor 100 at a predetermined distance for the stimulus to subtend a predetermined angle. Of course, the patient views the stimulus monocularly, with each eye tested separately. An operator may be seated at or near computer 80 for controlling the test parameters via a keyboard 120, or the testing may be fully automated. Referring to FIG. 5, the perimeter corresponding to the screen of color monitor 100 is preferably broken into four quadrants 140, 150, 160, 170, with a fixation target 130 moved into the outer corner of each of the four quadrants to access peripheral points in the patient's visual field. In this latter manner, the effective size of the screen is increased four-fold, allowing visual field testing to be performed for angles which would have required displays of much larger size.

Recall that color visual stimuli 40 can be displayed either at preprogrammed or manually selected locations within the patient's visual field. In accordance with the above test algorithm, computer 80 accordingly adjusts the saturation levels or modulation depth of the colors of color visual stimulus 40 to precisely determine the threshold level at which visual stimulus 40 is no longer observed. Glaucoma sufferers will typically require a much higher color saturation difference level. Recording the patient's response to the color visual stimuli provides a visual mapping of the patient's visual field, not unlike conventional perimetry.

Software to implement the above described visual field perimetry therefore includes displaying and varying the saturation levels of the color visual stimuli, monitoring the patient's fixation, recording the patient's response to the stimuli, and mapping the visual field on the basis of the patient's responses. Such software is readily capable of implementation by those skilled in the art who have been equipped with the understanding of the operation of the present invention as set forth herein, and may be written in C+, or any other programming language.

In addition to printing the test data on a printer 130 for each patient, either in graphical or text format, such test data may be saved on hard disk, recalled for later use, imported into a database for statistical analysis, and/or transmitted to a remote location.

Although the present invention has been realized and discussed in terms of displaying color visual stimulus 40 on color monitor 100, it is to be clearly understood that the present invention may have equally employed other types of displays, such as projection screens, LCDs, heads up displays (HUDs), total immersion displays, and the like. Also, the present invention may employ the multi-functional visual testing instrument of one of the applicants' copending application Ser. No. 09/146,655, which is incorporated herein by reference.

Figure 6:
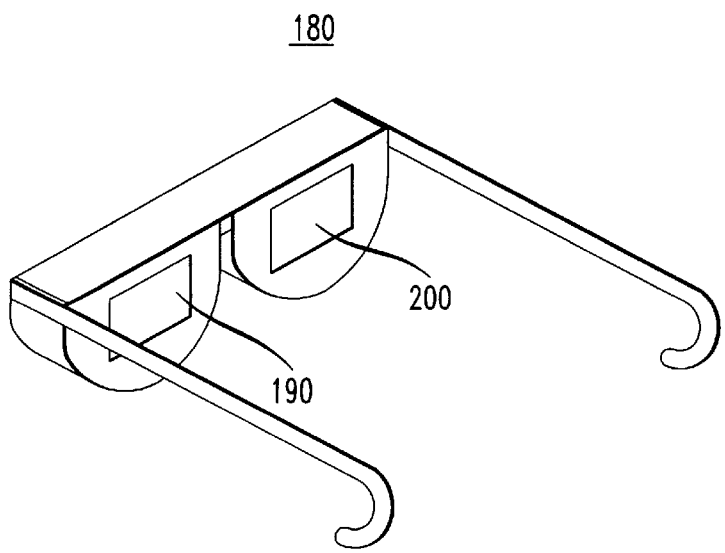
FIG. 6 depicts a close proximity display in the form of virtual reality glasses, which may be used by a patient to observe the color visual stimulus of FIG. 2.

Still further, as shown in FIG. 6, total immersion displays, such as close proximity displays in the form of virtual reality glasses 180, may be used to display color visual stimulus 40 to the patient, which advantageously may contain two independent displays 190, 200. See, for example, U.S. Pat. Nos. 5,565,949; and 5,737,060, which are incorporated herein by reference. In this latter case, both eyes can be tested at once by displaying color visual stimulus 40 to each eye independently. That is, color visual stimulus 40 is first displayed to right eye display 200 of virtual reality glasses 180, and then to left eye display 190, without the patient being able to distinguish which eye is being tested. Note that in this latter instance, the patient will view the fixation target binocularly. Similarly, testing may then be performed as discussed herein above.

It should be clearly understood that the embodiments herein are merely illustrative of the principles of the invention. Various modifications may be made by those skilled in the art which will embody the principles of the invention and fall within the spirit and the scope thereof. Furthermore, although the invention has been discussed in terms of its applicability to glaucoma, it is similarly believed that the present invention also has utility in testing for other retinal diseases and other eye disorders.

We claim:

1. A method of identifying those persons possibly suffering from glaucoma comprising the steps of:

displaying to a person a visual stimulus having gratings of different colors, the colors of the gratings alternating from a first to a second color at a desired temporal frequency, with the difference in the saturation levels of the colors being such that the person perceives the visual stimulus as having double the spatial frequency;

reducing the difference in the saturation levels of the colors until the person no longer perceives the visual stimulus; and comparing the difference in the saturation levels of the colors at which the person no longer perceives the visual stimulus with the difference in saturation levels at which a person with normal vision no longer perceives the visual stimulus.

2. The method of claim 1 wherein the first and second colors are isoluminent.

3. The method of claim 1 wherein the gratings are circular gratings.

4. The method of claim 1 wherein the first and second colors are complementary colors.

5. The method of claim 4 wherein the complementary colors are blue and yellow.

6. The method of claim 1 wherein the saturation levels of the colors vary sinusoidally along a first direction.

7. The method of claim 1 wherein the difference in the saturation levels of the colors is measured using the saturation modulation depth.

8. The method of claim 1 further comprising positioning the person in front of a display on which the visual stimulus is displayed at various locations corresponding to locations within the person's visual field.

9. The method of claim 1 wherein the person views the visual stimulus monocularly.

10. The method of claim 1 wherein the step of reducing the difference in the saturation levels comprises reducing the difference in the saturation levels by a predetermined fraction of the previous value until the person no longer perceives the visual stimulus, and then increasing the difference in the saturation levels in predetermined incremental steps until the person again perceives the frequency-doubled visual stimulus.

11. The method of claim 10 wherein the predetermined fraction is one-half.

12. The method of claim 1 wherein the step of displaying the visual stimulus to the person comprises displaying the visual stimulus at predetermined locations within the person's visual field.

13. The method of claim 1 further comprising the step of using a fixation target to fixate the person's central vision.

14. The method of claim 13 wherein the person views the fixation target binocularly.

15. The method of claim 13 further comprising the step of monitoring the person's fixation.

16. The method of claim 13 further comprising the step of moving the fixation target.

17. A method for detecting eye disease and disorders comprising the steps of:
displaying to a person a visual stimulus having a pattern of adjacent colors alternating at a predetermined temporal frequency, the saturation level of the colors varying along a predetermined direction between a maximum and minimum such that the person perceives the visual stimulus as having double the spatial frequency;
varying the saturation modulation depth of the colors; and
identifying those persons as possibly suffering from an eye disease or disorder who have more difficulty in observing the visual stimulus as the saturation modulation depth of the colors is reduced.

18. The method of claim 17 wherein the pattern includes circular gratings.

19. The method of claim 17 wherein the colors are isoluminent.

20. The method of claim 17 wherein the colors are complementary colors.

21. The method of claim 20 wherein the complementary colors are blue and yellow.

22. The method of claim 17 wherein the saturation levels of the colors vary sinusoidally along the predetermined direction.

23. The method of claim 17 further comprising the step of positioning the person in front of a display on which the visual stimulus is displayed at various locations corresponding to locations within the person's visual field.

24. The method of claim 17 wherein the person views the visual stimulus monocularly.

25. The method of claim 17 wherein the step of varying the saturation modulation depth comprises reducing the saturation modulation depth by a predetermined fraction of the previous value until the person no longer perceives the visual stimulus, and then increasing the saturation modulation depth in predetermined incremental steps until the person again perceives the frequency-doubled visual stimulus.

26. The method of claim 25 wherein the predetermined fraction is one-half.

27. The method of claim 17 wherein the step of displaying the visual stimulus to the person comprises displaying the visual stimulus at predetermined locations within the person's visual field.

28. The method of claim 17 further comprising the step of using a fixation target to fixate the person's central vision.

29. The method of claim 28 wherein the person views the fixation target binocularly.

30. The method of claim 28 further comprising the step of monitoring the person's fixation.

31. The method of claim 28 further comprising the step of moving the fixation target.

32. A method for detecting the loss of ganglion cells in the retina of a person comprising the steps of:
positioning the person in front of a display;
displaying on the display a visual stimulus having circular gratings with isoluminent colors alternating synchronously at a predetermined temporal frequency, the saturation levels of the colors varying sinusoidally radially inward between a maximum and minimum sufficient for the person to perceive the visual stimulus as having double the spatial frequency;
varying the difference between the maximum and minimum saturation levels of the colors;
recording as a saturation threshold the difference between the maximum and minimum saturation levels of the colors at which the person no longer perceives the visual stimulus; and
comparing the saturation threshold with that of a person with normal vision, wherein a substantially higher than normal saturation threshold is indicative of the loss of ganglion cells.

33. The method of claim 32 wherein the colors are a complementary color pair.

34. The method of claim 33 wherein the complementary color pair is blue and yellow.

35. The method of claim 32 wherein the step of varying the difference between the maximum and minimum saturation levels comprises reducing the difference by a predetermined fraction of the previous value until the person no longer perceives the visual stimulus, and then increasing the difference between the maximum and minimum saturation levels in predetermined incremental steps until the person again perceives the frequency-doubled visual stimulus.

36. The method of claim 35 wherein the predetermined fraction is one-half.

37. The method of claim 32 wherein the step of displaying the visual stimulus to the person comprises displaying the visual stimulus at predetermined locations within the person's visual field.

38. The method of claim 32 further comprising the step of using a fixation target to fixate the person's central vision.

39. The method of claim 38 wherein the person views the fixation target binocularly.

40. The method of claim 38 further comprising the step of monitoring the person's fixation.

41. The method of claim 38 further comprising the step of moving the fixation target.

42. A method of screening persons for glaucoma comprising the steps of:
fixating the person's central vision;
displaying to the person in a random manner and at predetermined locations within the patient's visual field a visual stimulus, the visual stimulus having a pattern of different colors, each alternating from a first to a second color at a desired temporal frequency, the saturation level of the colors varying between a maximum and minimum along a predetermined direction for the person to perceive the visual stimulus as having double the spatial frequency;
varying the difference between the maximum and minimum saturation levels of the color for each determined location; and
recording the difference between the maximum and minimum saturation levels at which the person no longer perceives the visual stimulus.

43. The method of claim 42 wherein the colors are isoluminent.

44. The method of claim 42 wherein the pattern includes circular gratings.

45. The method of claim 42 wherein the colors are complementary colors.

46. The method of claim 45 wherein the complementary colors are blue and yellow.

47. The method of claim 42 wherein the saturation levels of the colors vary sinusoidally along the predetermined direction.

48. The method of claim 42 wherein the difference in the saturation levels of the colors is expressed using the saturation modulation depth.

49. The method of claim 42 wherein the person views the visual stimulus monocularly.

50. The method of claim 42 wherein the step of varying the difference between the maximum and minimum saturation levels comprises reducing the difference by a predetermined fraction of the previous value until the person no longer perceives the visual stimulus, and then increasing the difference between the maximum and minimum saturation levels in predetermined incremental steps until the person again perceives the frequency-doubled visual stimulus.

51. The method of claim 50 wherein the predetermined fraction is one-half.

52. The method of claim 42 further comprising the step of comparing the difference in the maximum and minimum saturation levels at which the person no longer perceives the visual stimulus with the difference in maximum and minimum saturation levels at which a person with normal vision no longer perceives the visual stimulus.

53. A system for identifying those persons possibly suffering from glaucoma comprising:

a display;

means for displaying on said display a visual stimulus to a person, said visual stimulus having gratings of different colors, the colors of the gratings alternating from a first to a second color at a desired temporal frequency, with the difference in the saturation levels of the colors being such that the person perceives the visual stimulus as having double the spatial frequency;

means for reducing the difference in the saturation levels of the colors until the person no longer perceives the visual stimulus; and means for comparing the difference in the saturation levels of the colors at which the person no longer perceives the visual stimulus with the difference in saturation levels at which a person with normal vision no longer perceives the visual stimulus.

54. The system of claim 53 wherein the first and second colors are isoluminent.

55. The system of claim 53 wherein the gratings are circular gratings.

56. The system of claim 53 wherein the first and second colors are complementary colors.

57. The system of claim 56 wherein the complementary colors are blue and yellow.

58. The system of claim 53 wherein the saturation levels of the first and second colors vary sinusoidally along a first direction.

59. The system of claim 53 wherein the difference in the saturation levels of the colors is expressed using the saturation modulation depth.

60. The system of claim 53 wherein the person views the visual stimulus monocularly.

61. The system of claim 53 wherein the difference in the saturation levels of the colors is reduced by a predetermined fraction of the previous value until the person no longer perceives the visual stimulus, and then is increased in predetermined incremental steps until the person again perceives the frequency-doubled visual stimulus.

62. The system of claim 61 wherein the predetermined fraction is one-half.

63. The system of claim 53 wherein the visual stimulus is displayed at predetermined locations within the person's visual field.

64. The system of claim 53 further including means for fixating the person's central vision.

65. The system of claim 64 wherein said means for fixating includes a fixation target.

66. The system of claim 65 wherein the person views the fixation target binocularly.

67. The system of claim 65 wherein said fixation target is moving.

68. The system of claim 65 wherein said means for fixating includes means for monitoring the person's fixation.

69. The system of claim 53 wherein said means for displaying includes a computer.

70. The system of claim 53 further comprising means for recording the person's response to the visual stimulus.

71. A system for screening persons for glaucoma comprising the steps of:

means for fixating the person's central vision;

means for displaying to the person in a random manner and at predetermined locations within the patient's visual field a visual stimulus, the visual stimulus having a pattern of different colors, each alternating from a first to a second color at a desired temporal frequency, the saturation level of the colors varying between a maximum and minimum along a predetermined direction for the person to perceive the visual stimulus as having double the spatial frequency;

means for varying the difference between the maximum and minimum saturation levels of the color for each determined location; and means for recording the difference between the maximum and minimum saturation levels at which the person no longer perceives the visual stimulus.

72. The system of claim 71 wherein the colors are isoluminent.

73. The system of claim 71 wherein the pattern includes circular gratings.

74. The system of claim 71 wherein the colors are complementary colors.

75. The system of claim 74 wherein the complementary colors are blue and yellow.

76. The system of claim 71 wherein the saturation levels of the colors vary sinusoidally along the predetermined direction.

77. The system of claim 71 wherein the difference in the saturation levels of the color is expressed using the saturation modulation depth.

78. The system of claim 71 wherein the person views the visual stimulus monocularly.

79. The system of claim 71 wherein the difference between the maximum and minimum saturation levels is reduced by a predetermined fraction of the previous value until the person no longer perceives the visual stimulus, and then is increased in predetermined incremental steps until the person again perceives the frequency-doubled visual stimulus.

80. The system of claim 79 wherein the predetermined fraction is one-half.

81. The system of claim 71 wherein said means for displaying includes a computer.

82. The system of claim 71 wherein said means of recording includes a computer mouse.

83. The system of claim 71 wherein said means for fixating includes a fixation target.

84. The system of claim 83 wherein the person views the fixation target binocularly.

85. The system of claim 83 wherein said fixation target is moving.

86. The system of claim 71 wherein said means for fixating includes means for monitoring the person's fixation.

* * * * *